(12) United States Patent
Cayea (10) Patent No.: US 12,053,361 B2
(45) Date of Patent: Aug. 6, 2024

(54) MULTIPURPOSE EMERGENCY PREPAREDNESS SYSTEM

(71) Applicant: Brenda Cayea, Modesto, CA (US)

(72) Inventor: Brenda Cayea, Modesto, CA (US)

( * ) Notice: Subject to any disclaimer, the term of this patent is extended or adjusted under 35 U.S.C. 154(b) by 0 days.

(21) Appl. No.: 17/946,646

(22) Filed: Sep. 16, 2022

(65) Prior Publication Data
US 2024/0091080 A1 Mar. 21, 2024

(51) Int. Cl.
*A61F 17/00* (2006.01)

(52) U.S. Cl.
CPC .................................. *A61F 17/00* (2013.01)

(58) Field of Classification Search
CPC ........ A61F 17/00; A61F 15/00; A61F 15/001; B65D 65/463; B65D 65/466
USPC ............... 206/223, 546, 570, 803, 811, 828; 426/138, 279
See application file for complete search history.

(56) References Cited

U.S. PATENT DOCUMENTS

| | | | | |
|---|---|---|---|---|
| 1,509,194 A * | 9/1924 | Dresser | .................. | A23G 9/506 426/94 |
| 3,951,260 A * | 4/1976 | Frazee | .................. | A62B 99/00 116/210 |
| 5,011,020 A * | 4/1991 | Stevens | .................. | A45C 13/02 206/811 |
| 6,454,097 B1 * | 9/2002 | Blanco | ..................... | A61F 17/00 206/570 |
| 7,628,275 B2 * | 12/2009 | Smith | ..................... | A62B 99/00 206/570 |
| 8,167,130 B2 * | 5/2012 | Holstein | ................. | A61F 17/00 206/499 |
| 8,647,123 B1 * | 2/2014 | Carter | ..................... | G16H 40/63 434/262 |
| 2007/0007164 A1 * | 1/2007 | Lord | ..................... | A61J 7/0084 206/581 |
| 2011/0114516 A1 * | 5/2011 | Vahlkamp | .............. | B65D 77/04 5/636 |
| 2013/0167857 A1 * | 7/2013 | DeGeorge | ................ | A45D 7/04 206/229 |
| 2014/0061273 A1 * | 3/2014 | Bullivant | ................. | A45F 3/04 224/576 |
| 2014/0161944 A1 * | 6/2014 | Briganti | ............... | B65D 65/463 426/138 |
| 2015/0223586 A1 * | 8/2015 | Mather | ..................... | A45F 3/04 206/232 |
| 2016/0090228 A1 * | 3/2016 | Soria | ..................... | A47K 10/38 206/233 |
| 2017/0275070 A1 * | 9/2017 | Solomon | .............. | B65D 81/052 |
| 2020/0289231 A1 * | 9/2020 | Gustafson | ................. | A45F 4/02 |

* cited by examiner

*Primary Examiner* — J. Gregory Pickett
*Assistant Examiner* — Jenine Pagan (57) ABSTRACT

A multipurpose emergency preparedness system may be provided. The system may utilize an exterior packaging layer forming a fluid-tight seal around an inner packaging layer. The inner packaging layer may have a plurality of perimeter retaining walls defining one or more cavities therein. The system may further utilize a plurality of survival kits disposed within the one or more cavities. The system may have a plurality of emergency preparedness items disposed within each of the plurality of survival kits.

20 Claims, 5 Drawing Sheets

MULTIPURPOSE EMERGENCY PREPAREDNESS SYSTEM

BACKGROUND OF THE INVENTION

Throughout recorded time, the human populous has been plagued by periodic disasters, on both macro and micro scales, that trigger emergency situations. Such circumstances can determine life or death for the individuals facing the emergency. Given the value of human life, some individuals place great value on being prepared for such emergency situations. Over time, the mentality for such individuals has arisen that it is better to be prepared and not need the preparation than to not be prepared and need it.

While emergency situations are statistically rare both on the macro and micro scales, global disaster has shown to repeat itself with a rhythmic periodicity. For instance, in the United States alone, major war has been experienced roughly every 80 years spanning the Revolutionary War, the Civil War and World War II. Current global trends could precipitate a new global conflict wages with modern modes of warfare that could trigger another global disaster where the least well-off of the populous is the hardest hit. Therefore, it would be advantageous to provide a means of preparing these individuals for such a global catastrophe in a way that is affordable for this segment of society.

Beyond global disaster on the macro scale, emergency situations arise periodically throughout the lives of most people on the micro scale. Many news stories circulate about hikers getting stranded in the wilderness, deep sea divers being left behind in the ocean, plane crash victims facing survival situations, residential fires requiring quick-thinking survival tactics for escape and the like. Such situations have been popularized in the culture through dramatic cinematic films where the protagonist is underprepared for the emergency situation and must improvise to survive against the antagonist of mother nature. Given the diversity of emergency situation that may be faced by the individual, e.g. land, water, fire, air-based emergencies etc., it would be advantageous to provide an emergency preparedness system that addresses the most common of these emergency situations with potential survival solutions in the broadest manner possible.

In response to the general public becoming aware of potential macro and micro scale disasters, the global disaster preparedness industry has been estimated to be valued at over 100 billion dollars. Nationally, the disaster preparedness industry is estimated to be valued at over 14 billion dollars in the United States alone. However, many of the disaster preparedness solutions in existence are directed towards providing survival solutions to global disaster situations over a long period of time and therefore carry large costs to the individual. Therefore, it would be advantageous to provide a multipurpose emergency preparedness system that addresses local emergency situations in the short term for the individual who does not have a large budget for preparedness.

While in an emergency situation, the individual may not be considering the impact upon their surrounding environment when using an emergency preparedness kit to find survival solutions. However, this does not mean that a manufacturer of such emergency preparedness kits cannot contemplate environmental impacts. For instance, such kits are often designed to be single-use or at least contain packaging that is disposable upon use. Given the life-threatening situations that individuals will face when using an emergency preparedness kit, they likely will not be considering the most environmentally-conscious means of disposing of such packaging or single-use contents. Further, a consumer purchasing such a kit prior to the emergency situation will often consider environmental factors when making their purchase given the trend of eco-consciousness. Therefore, it would be advantageous to provide a multipurpose emergency preparedness kit that utilizes as many sustainable and/or biodegradable materials as possible in its manufacture.

Additionally, such emergency situations most often occur when an individual is in the midst of traveling away from home when transport of the emergency preparedness kit can be a burden to varying degree. Therefore, the form factor and weight of the kit is advantageously minimized to reduce any potential burden of transport. However, by minimizing the form factor and weight, a constraint is placed upon the survival solution contents that may be placed into the kit. Therefore, it would be advantageous to provide an emergency preparedness system that comprises dual-use elements such as product packaging that may be used for as a food source, a fuel source, a first aid source and the like.

DETAILED DESCRIPTION OF THE INVENTION

Before describing the present invention in detail, it is to be understood that the invention is not limited to any one of the particular embodiments, which of course may vary. It is also to be understood that the terminology used herein is for the purpose of describing particular embodiments only, and therefore is not necessarily intended to be limiting. As used in this specification and the appended claims, terms in the singular and the singular forms "a," "an," and "the" include plural referents unless the context clearly dictates otherwise. Thus, for example, reference to "a multipurpose emergency preparedness system" also includes a plurality of multipurpose emergency preparedness systems and the like.

In some embodiments, a multipurpose emergency preparedness system, is provided comprising an exterior packaging layer forming a fluid-tight seal around an inner packaging layer; the inner packaging layer comprises a plurality of perimeter retaining walls defining one or more cavities therein; a plurality of survival kits disposed within the one or more cavities; and a plurality of emergency preparedness items disposed within each of the plurality of survival kits.

In some embodiments, the exterior packaging layer is fabricated from a transparent material.

In some embodiments, the exterior packaging layer is fabricated from a flexible material.

In some embodiments, the exterior packaging layer is fabricated from a biodegradable material having one or more alternative-use characteristics.

In some embodiments, the inner packaging layer is fabricated from an opaque material.

In some embodiments, the inner packaging layer is fabricated from a rigid material.

In some embodiments, the inner packaging layer is fabricated from a material comprising one or more medicinal compounds.

In some embodiments, the inner packaging layer is fabricated from a biodegradable material having one or more alternative-use characteristics.

In some embodiments, the plurality of perimeter retaining walls enclose a plurality of interior retaining walls.

In some embodiments, the plurality of interior retaining walls comprise a horizontal portion and a vertical portion.

In some embodiments, each of the plurality of survival kits comprise an emergency kit packaging layer.

In some embodiments, the emergency kit packaging layer is fabricated from a biodegradable material having one or more alternative-use characteristics.

In some embodiments, the emergency kit packaging layer encloses the plurality of emergency preparedness items.

In some embodiments, each of the plurality of survival kits comprise an emergency indicia element disposed upon an exterior surface of the emergency kit packaging layer.

In some embodiments, the plurality of survival kits comprise a land-based emergency kit comprising a water purification instrument, a metallic thermal blanket, a fire starter device, a fireproof covering element and a smoke filtering mask.

In some embodiments, the plurality of survival kits comprise a water-based emergency kit comprising an inflatable buoy device, a thermal blanket and a ginger food item.

In some embodiments, the plurality of survival kits comprise a fire-based emergency kit comprising a fireproof covering element and a smoke filtering mask.

In some embodiments, the plurality of survival kits comprise a flight-based emergency kit comprising an inflatable buoy device, a water purification instrument, a metallic thermal blanket, a fire starter device, a fireproof covering element, a ginger food item and a smoke filtering mask.

In some embodiments, a multipurpose emergency preparedness system is provided comprising an outer packaging layer forming a fluid-tight seal around an inner packaging layer; the inner packaging layer comprises a plurality of perimeter retaining walls defining one or more cavities therein, wherein the plurality of perimeter retaining walls enclose a plurality of interior retaining walls; a plurality of survival kits disposed within the one or more cavities, wherein: each of the plurality of survival kits comprise an emergency kit packaging layer, and each of the plurality of survival kits comprise an emergency indicia element disposed upon an exterior surface of the emergency kit packaging layer; and a plurality of emergency preparedness items disposed within each emergency kit packaging layer.

In some embodiments, a multipurpose emergency preparedness system is provided comprising an outer packaging layer forming a fluid-tight seal around an inner packaging layer; the inner packaging layer comprises a plurality of perimeter retaining walls defining one or more cavities therein, wherein: the plurality of perimeter retaining walls enclose a plurality of interior retaining walls, and the plurality of interior retaining walls comprise a horizontal portion and a vertical portion; a plurality of survival kits disposed within the one or more cavities, wherein: each of the plurality of survival kits comprise an emergency kit packaging layer, and each of the plurality of survival kits comprise an emergency indicia element disposed upon an exterior surface of the emergency kit packaging layer; and a plurality of emergency preparedness items disposed within each emergency kit packaging layer.

Figure 1:
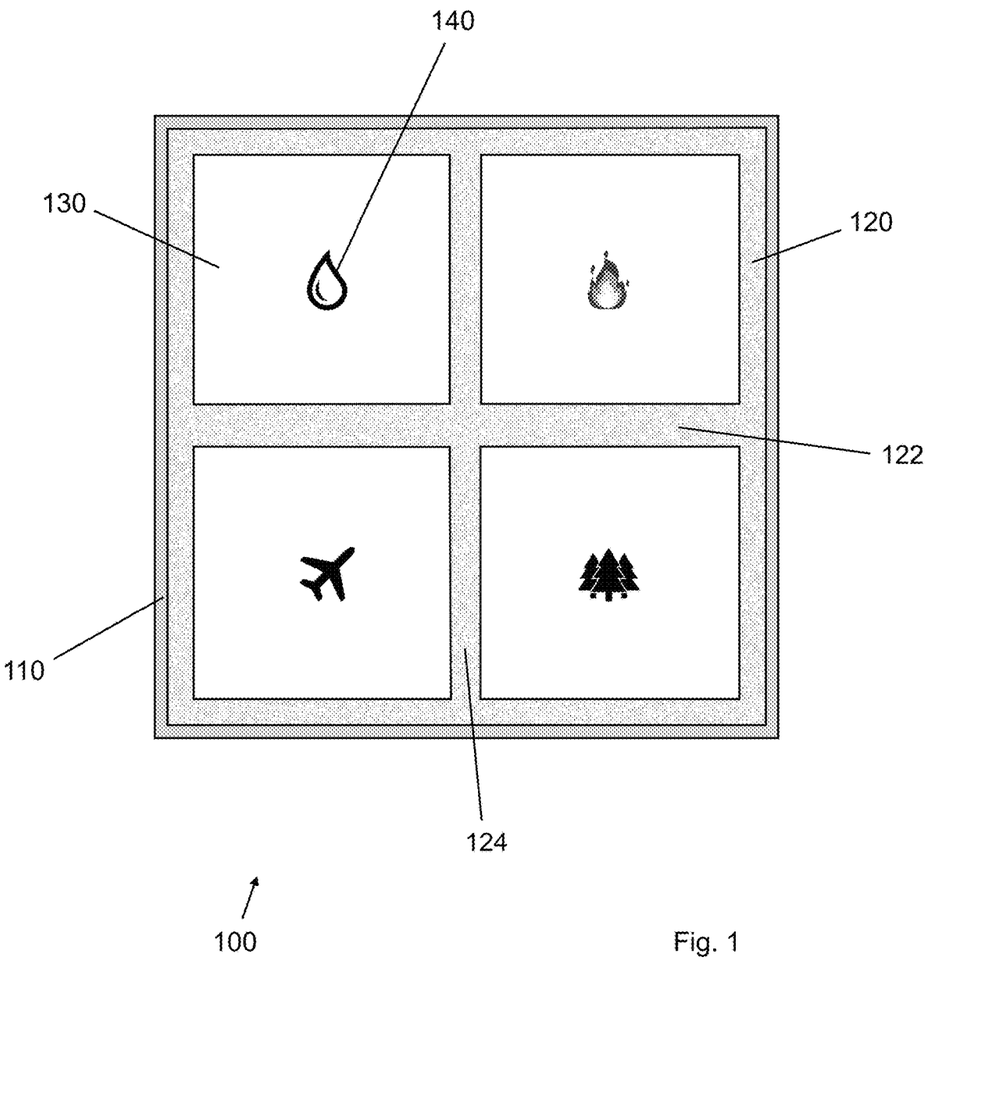
FIG. 1 illustrates an overview of a multipurpose emergency preparedness system with four distinct survival kits in accordance with some embodiments of the present invention.

Exemplary embodiments of the present invention are illustrated in the accompanying figures. As shown in FIG. 1, an overview of a multipurpose emergency preparedness system 100 with four distinct survival kits 130 is provided. The multipurpose emergency preparedness system 100 may comprise an outer packaging layer 110, an inner packaging layer 120, a plurality of survival kits 130 and a plurality of emergency indicia 140.

The outer packaging layer 110 may be utilized as a lid and/or a fluid-sealing layer for the multipurpose emergency preparedness system 100. Therefore, the outer packaging layer 110 may be used as a disposable packaging layer upon accessing the plurality of survival kits 130 contained therein. Accordingly, the outer packaging layer 110 may exhibit fluid-sealing characteristics and may be made from one or more environmental materials. Thereby, the disposable nature of the outer packaging layer 110 may not have a detrimental impact upon the surrounding environment in which the system 100 is being used, but rather may have one or more alternative-use characteristics.

The inner packaging layer 120 may be enclosed within the outer packaging layer 110 and so may not be designed to be fluid-sealing but, rather, may be structured from an opaque robust material designed to provide structural support for the packaging of the system 100. Further, the inner packaging layer 120 may comprise a perimeter portion that is disposed adjacent the outer packaging layer 110 and the survival kits 130 as shown in FIG. 1. The perimeter portion may enclose a horizontal portion 122 and a vertical portion 124 of the inner packaging layer 120. The horizontal portion 122 and the vertical portion 124 together may form a cross-shaped structure which together with the perimeter portion may define four individual cavities therein for retaining the plurality of survival kits 130. While the inner packaging layer 120 may not be immediately disposed of by the user until all survival kits 130 are used, the layer 120 is still designed to be disposable and, thereby, may be made from one or more environmental materials that may not have a detrimental impact upon the surrounding environment in which the system 100 is being used, but rather may have one or more alternative-use characteristics.

Each of the survival kits 130 may comprise their own layer of product packaging which may take the form of an opaque semi-flexible packaging layer in the shape of a box. The product packaging of each survival kit 130 may contain a set of emergency preparedness items therein. Each set of emergency preparedness items may be associated with a specific category of emergency event. For instance, a separate of emergency preparedness items may be created for categories of emergency events including, but not limited to, land-based emergencies, water-based emergencies, fire-based emergencies, flight-based emergencies and the like or any combinations thereof. Each set of emergency preparedness items may be packaged within their own survival kit 130 product packaging.

Further, each set of emergency preparedness items may themselves be packaged within a disposable transparent fluid-sealing packaging arrangement in order to allow the user to see which emergency preparedness item is which while still maintaining a sanitary fluid-seal around each item. Since the transparent fluid-sealing packaging of each item is designed to be single-use and disposable, this packaging may similarly be made from one or more environmental materials that may not have a detrimental impact upon the surrounding environment in which the system 100 is being used, but rather may have one or more alternative-use characteristics.

Each survival kit 130 may comprise one or more emergency indicia 140 displayed upon an exterior top surface thereof as shown in FIG. 1. The emergency indicia 140 may be visually associated with a specific category of emergency event. For instance, a water drop symbol may be utilized to indicate that water-based emergency preparedness items are contained therein, a fire plume symbol may be utilized to indicate that fire-based emergency preparedness items are contained therein, an airplane symbol may be utilized to indicate that flight-based emergency preparedness items are contained therein, a tree forest symbol may be utilized to indicate that land-based emergency preparedness items are contained therein and the like or any combinations thereof.

In some embodiments, each of the emergency indicia 140 may comprise a light-reflective material that may take the form of a micro-prismatic material, a glass bead reflective material and like material exhibiting total internal reflection characteristics or any combination thereof. In some embodiments, each of the emergency indicia 140 may comprise one or more luminescent materials that may take the form of zinc sulfide or strontium aluminate-containing compounds. Such light-reflective and/or luminescent materials would be advantageous to utilize in many emergency situations where the user is stranded in a remote area without means of communication with emergency personnel. Light-reflective material may allow the user to be more easily located by emergency personnel during a search and rescue operation.

The term 'environmental materials' as used in this context and throughout this disclosure document is intended to connote any material that is environmentally-friendly and, specifically, that exhibits biodegradable and/or alternative-use characteristics. The term 'alternative-use characteristics' as used in this context and throughout this disclosure document is intended to connote any characteristic of a material that allows the given material to be secondarily used as a food source, a fuel source, a first aid source and the like or any combination thereof.

Such environmental materials may include, but are not limited to, gelatin, starch, cellulose, hemp, wood, cotton, bamboo, brown seaweed, beeswax, jojoba, sugarcane, corn, corn husk, mushroom byproduct, coconut shell, coconut husk and any derivative materials processed therefrom or any combination thereof. Specifically, these materials may be processed into one or more of transparent flexible wrapping layers, hydrophobic fluid-sealing layers, opaque robust support packaging, opaque semi-flexible packaging layers and the like or any combinations thereof.

In use, the one or more layers of product packaging of the multipurpose emergency preparedness system 100 including the outer packaging layer 110, the inner packaging layer 120, the plurality of survival kit 130 packaging layers, and the individual emergency preparedness item packaging may be disposed of within the surrounding environment of use and fully biodegrade. In this context, the term 'fully biodegrade' connotes the ability for a material to completely decompose within the timeframe of a single year which is advantageous in reducing the long-term pollution and littering of the environment while still accounting for the material's primary use as a packaging material for the system 100.

In some embodiments, the one or more layers of product packaging of the system 100 may be used as an emergency fuel source. In order to be viably used as a fuel source, one or more layers of product packaging of the system 100 may comprise a caloric value of at least 5 mega-Joules per kilogram, but preferably at least 10 mega-Joules per kilogram in order to provide a longer-burning fuel source such as hemp, wood, bamboo, corn husk, coconut shell, coconut husk and any derivative materials processed therefrom while still accounting for the material's primary use as a disposable packaging material for the system 100.

In some embodiments, the one or more layers of product packaging of the system 100 may be used as an emergency food source for packaging materials comprising bamboo, brown seaweed, beeswax, sugarcane, corn, mushroom byproduct and any derivative materials processed therefrom which each comprise a caloric value of at least 10 Joules per kilogram. This level of caloric density provides the user with a high enough level of energy for survival situations while still providing primary functionality as a disposable packaging material for the system 100.

In some embodiments, the one or more layers of product packaging of the system 100 may be used as an emergency first aid source for packaging materials comprising hemp, bamboo, seaweed, beeswax, mushroom byproduct, coconut shell, coconut husk and any derivative materials processed therefrom which all comprise one or more medicinal compounds that provide varying first aid functionality including, but not limited to, antibacterial, antifungal, antiviral, antiparasitic, antimicrobial, UV-reflection, pain-relief, inflammation, wound treatment, burn treatment, rash treatment and the like or any combination thereof. Specifically, the high-density form that these materials may take as packaging materials for the system may be better accessed as a first aid source via brewing the materials in hot water in order to extract out the medicinal benefits therefrom.

Figure 2:
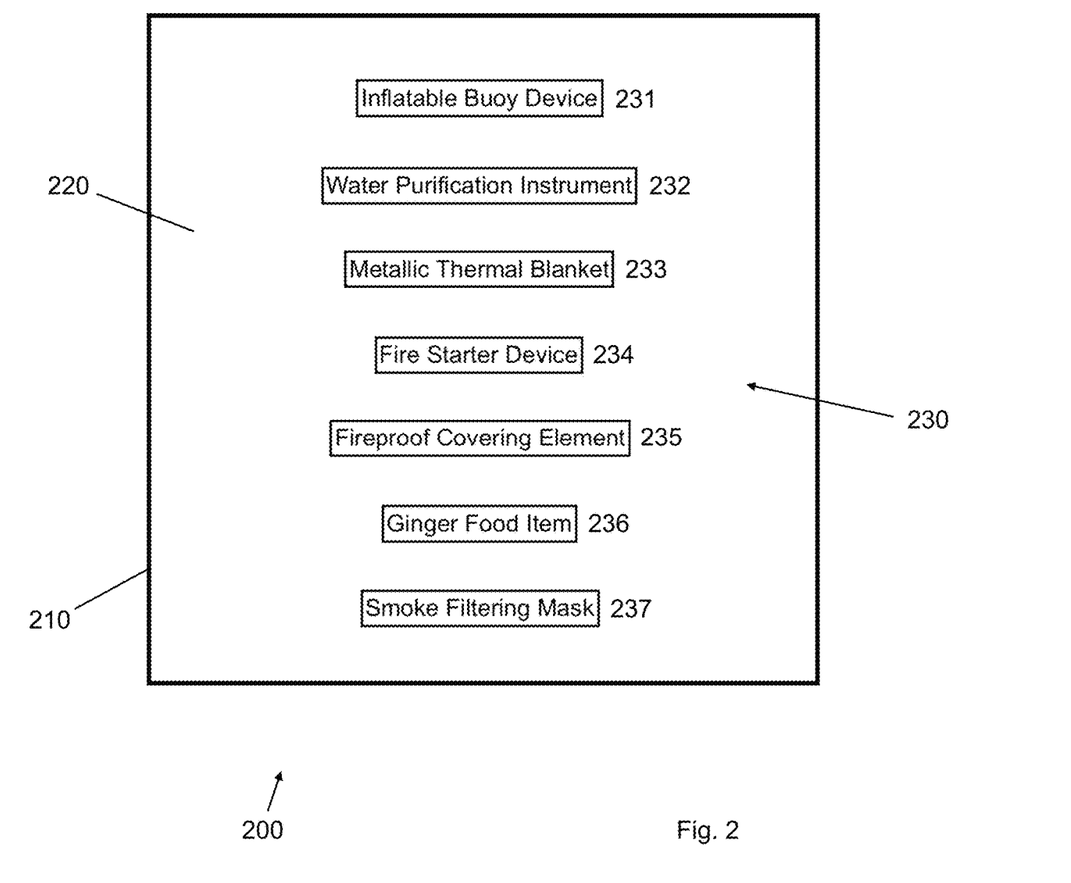
FIG. 2 illustrates a detailed view of a plurality of emergency preparedness items of one or more survival kits of a multipurpose emergency preparedness system in accordance with some embodiments of the present invention.

As shown in FIG. 2, a detailed view of a plurality of emergency preparedness items 230 of one or more survival kits 200 of a multipurpose emergency preparedness system is provided. The one or more survival kits 200 may comprise a layer of kit product packaging 210 that defines a cavity 220 therein which contains the plurality of emergency preparedness items 230 therein. The plurality of emergency preparedness items 230 may comprise, but are not limited to, an inflatable buoy device 231, a water purification instrument 232, a metallic thermal blanket 233, a fire starter device 234, a fireproof covering element 235, a ginger food item 236, a smoke filtering mask 237 and the like or any combination thereof.

The inflatable buoy device 231 may be advantageous in situations where water-related disasters may be encountered such as a visit to the beach, a boat trip, a cruise vacation, over-water air travel, a water park visit, crossing a river and the like. The water purification instrument 232 may be advantageous in situations where potable water is scarce such as drought environments, desert environments, microbial-rich water environments, long hikes outdoors, extended camping trips and the like. The metallic thermal blanket 233 may be advantageous in situations where temperature is a concern such as cold weather environments, overnight chill environments, desert environments, indoor cold facilities and the like. The fire starter device 234 may be advantageous in situations where emergency cooking, heating and lighting may be required such as in extended wilderness trips, search and rescue situations, travel through cold weather environments and the like. The fireproof covering element 235 may be advantageous in situations where fire is a hazard such as in residential or industrial fire events, vehicular fire events, wildfire or forest fire events, travel through drought-ridden areas and the like. The ginger food item 236 may be advantageous in situations where nausea-related events are encountered such as air travel, extended car travel, pregnancy sickness, boat trips, elevation change events, vertigo afflictions, amusement park rides and the like. The smoke filtering mask 237 may be advantageous in situations where fire or smoke-related environments are encountered such as in residential or industrial fire events, vehicular fire events, wildfire or forest fire events, travel through drought-ridden areas and the like.

While the plurality of emergency preparedness items 230 are illustrated in FIG. 2 as being contained within a single survival kit 200, it is understood that the items 230 may be separated into categorically-similar groups and packaged into separate survival kits 200 by such grouping. For instance, the inflatable buoy device 231, the thermal blanket 233 and the ginger food item 236 may be included in a survival kit 200 containing water-based emergency preparedness items. The fireproof covering element 235 and the smoke filtering mask 237 may be included in a survival kit 200 containing fire-based emergency preparedness items. All of the emergency preparedness items 230 illustrated in FIG. 2 may be included in a survival kit 200 containing flight-based emergency preparedness items given the variability and diversity of emergency situations that may be faced during a flight-based disaster situations. The water purification instrument 232, the metallic thermal blanket 233, the fire starter device 234, the fireproof covering element 235 and the smoke filtering mask 237 may be included in a survival kit 200 containing land-based emergency preparedness items. Such categorical separation of the emergency preparedness items 230 into separate survival kits 200 may be accomplished according to the embodiment illustrated in FIG. 1 and the associated emergency indicia 140 pertaining to land-based emergencies, water-based emergencies, fire-based emergencies, flight-based emergencies and the like.

Figure 3:
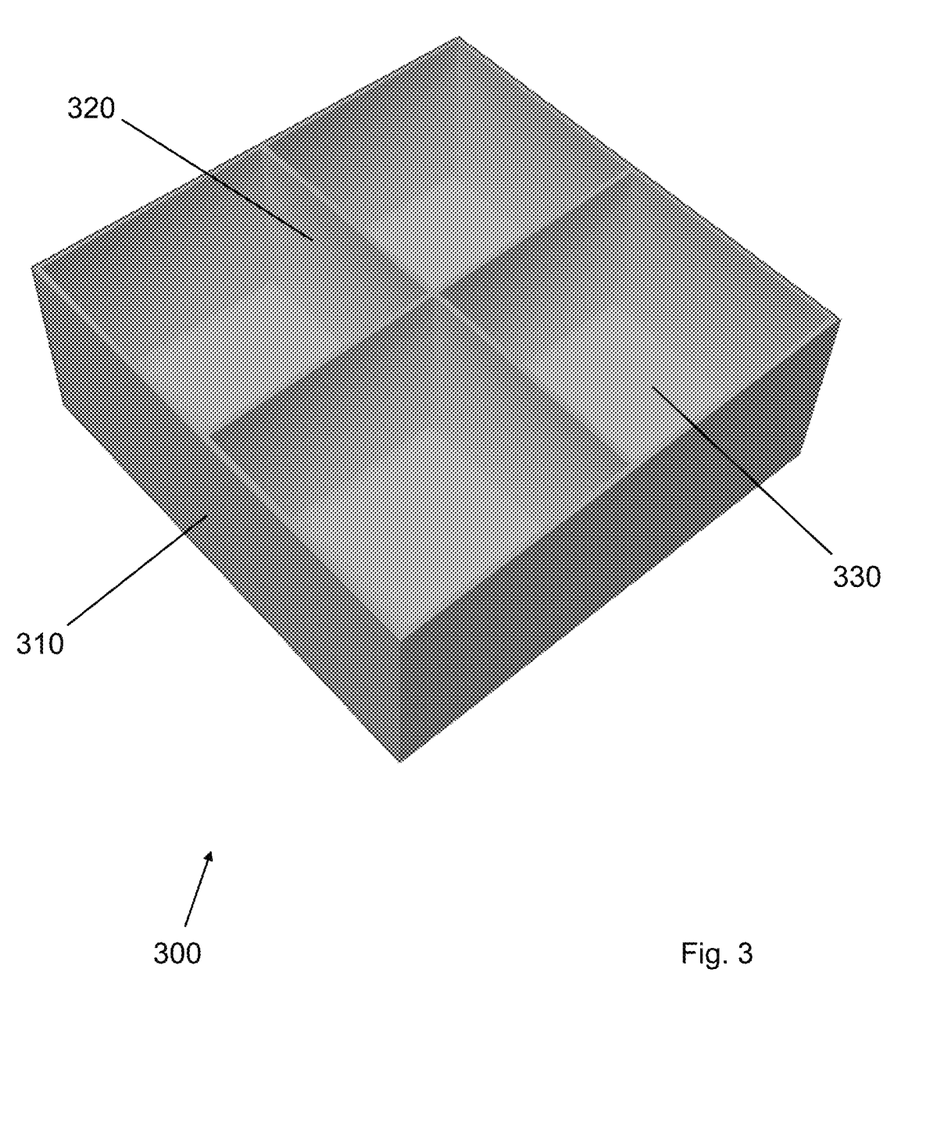
FIG. 3 illustrates a perspective view of an inner layer of product packaging for four distinct survival kits of a multipurpose emergency preparedness system in accordance with some embodiments of the present invention.

As shown in FIG. 3, a perspective view of an inner layer of product packaging 300 for four distinct survival kits of a multipurpose emergency preparedness system is provided. The inner layer of product packaging 300 may comprise a plurality of exterior retaining walls 310, a plurality of interior retaining walls 320 and a plurality of cavities 330 defined thereby. The plurality of exterior and interior retaining walls 310, 320 may be structured to retain one or more survival kits within respective cavities 330 as illustrated in FIG. 1.

While the exterior retaining walls 310 may suffice in retaining the survival kits within the product packaging 300 without the need of the interior retaining walls 320, the interior retaining walls 320 are advantageous in serving to physically separate the various survival kits from one another which allows the user to more easily identify one kit from another in an emergency situation where such discrimination becomes difficult. Additionally, the interior retaining walls 320 prevent the various survival kits from moving within the exterior retaining walls 310 and perhaps becoming damaged.

Further, the interior retaining walls 320 provide additional emergency survival materials that may have alternative-use characteristics as an emergency fuel source, an emergency food source, an emergency first aid source and the like or any combination thereof. Therefore, while the industry of packaging seeks to minimize materials utilized, the present invention finds benefit in utilizing additional environmental materials for packaging given their alternative-use characteristics in the various emergency situations faced by the user.

Figure 4:
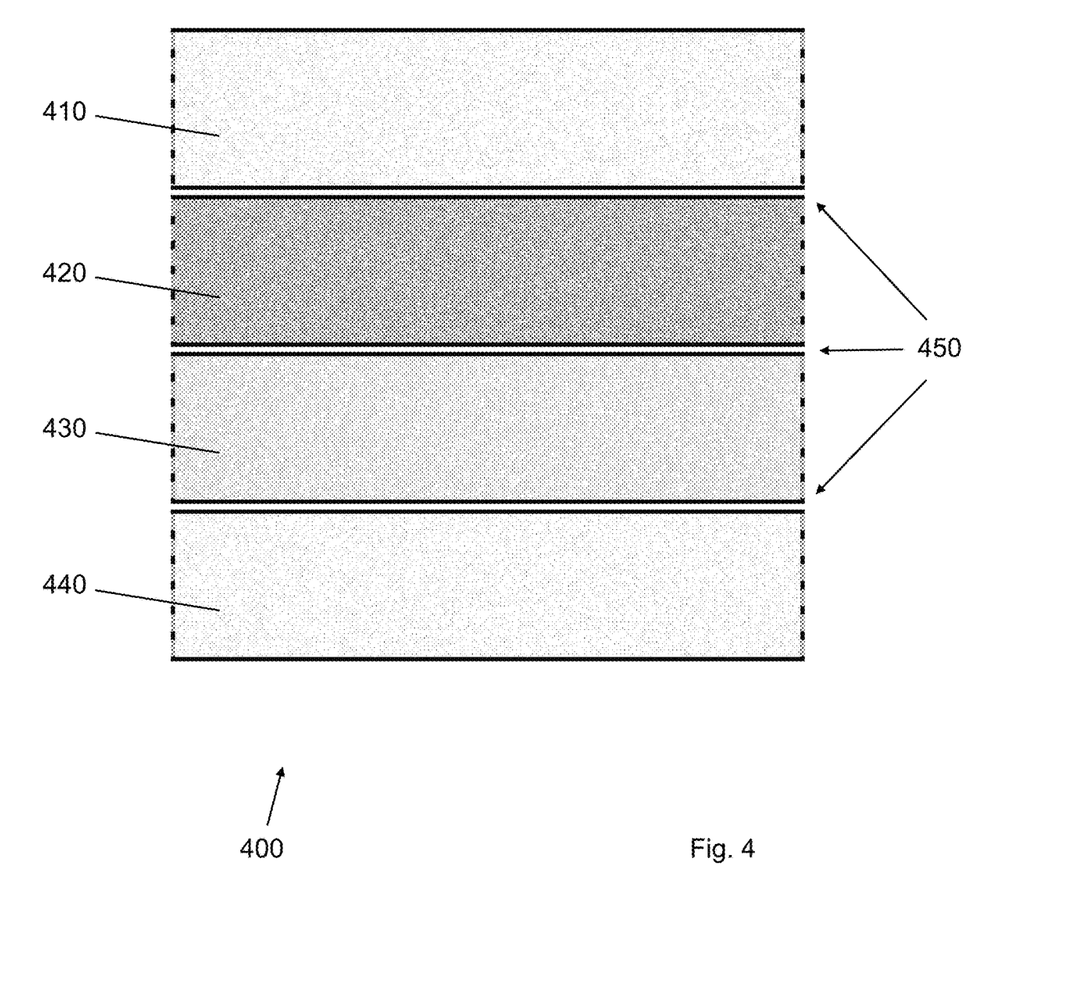
FIG. 4 illustrates a cross-sectional view of a multilayer packaging configuration of a multipurpose emergency preparedness system in accordance with some embodiments of the present invention.

As shown in FIG. 4, a cross-sectional view of a multilayer packaging configuration 400 of a multipurpose emergency preparedness system is provided. The multilayer packaging configuration 400 may comprise an exterior packaging layer 410, an inner layer of product packaging 420, an emergency kit packaging layer 430, an emergency preparedness item packaging layer 440 and one or more air gaps 450 disposed between each packaging layer as shown in FIG. 4.

The exterior packaging layer 410 may be utilized as a means of fluid-sealing the entirety of a multipurpose emergency preparedness system and thereby protecting it from environmental contamination before initial use. Therefore, the exterior packaging layer 410 may be advantageously fabricated as a disposable, transparent, and flexible fluid-sealing packaging layer. Further, given the disposable nature of the exterior packaging layer 410, it may be made from one or more environmental materials with alternative-use characteristics. Specifically, the one or more environmental materials used in fabricating the exterior packaging layer 410 may include, but are not limited to, gelatin, seaweed, cotton, beeswax, jojoba and any derivative materials processed therefrom or any combination thereof.

The inner layer of product packaging 420 may be utilized as a means of robustly retaining a plurality of survival kits within respective cavities (that may be defined by the inner layer of product packaging) of a product packaging of a multipurpose emergency preparedness system and, thereby, protecting the structural integrity of the survival kits and the emergency preparedness items contained therein. Therefore, the inner layer of product packaging 420 may be advantageously fabricated as a robust, opaque, and rigid load-bearing packaging layer. Further, given the survivalist use-cases for the multipurpose emergency preparedness system, the inner layer of product packaging 420 may be made from one or more environmental materials with alternative-use characteristics. Specifically, the one or more environmental materials used in fabricating the inner layer of product packaging 420 may include, but are not limited to, gelatin, starch, cellulose, hemp, wood, cotton, bamboo, beeswax, mushroom byproduct, coconut shell, coconut husk and any derivative materials processed therefrom or any combination thereof.

The emergency kit packaging layer 430 may be utilized as a means of retaining a plurality of emergency preparedness items within a cavity (that may be defined by the emergency kit packaging layer) of a survival kit and, thereby, protecting the structural integrity of the emergency preparedness items. Therefore, the emergency kit packaging layer 430 may be advantageously fabricated as an opaque semi-flexible packaging layer. Further, given the survivalist use-cases for the multipurpose emergency preparedness system, the emergency kit packaging layer 430 may be made from one or more environmental materials with alternative-use characteristics. Specifically, the one or more environmental materials used in fabricating the emergency kit packaging layer 430 may include, but are not limited to, gelatin, starch, cellulose, hemp, wood, cotton, bamboo, beeswax, mushroom byproduct, coconut shell, coconut husk and any derivative materials processed therefrom or any combination thereof.

The emergency preparedness item packaging layer 440 may be utilized as a means of fluid-sealing an emergency preparedness item in order to protect the sanitary use thereof and, thereby, a plurality of layers 440 may be utilized in order to fluid-seal respective emergency preparedness items. Therefore, the emergency preparedness item packaging layer 440 may be advantageously fabricated as a disposable, transparent, and flexible fluid-sealing packaging layer. Further, given the disposable nature of the emergency preparedness item packaging layer 440, it may be made from one or more environmental materials with alternative-use characteristics. Specifically, the one or more environmental materials used in fabricating the emergency preparedness item packaging layer 440 may include, but are not limited to, gelatin, seaweed, cotton, beeswax, jojoba and any derivative materials processed therefrom or any combination thereof.

Figure 5A:
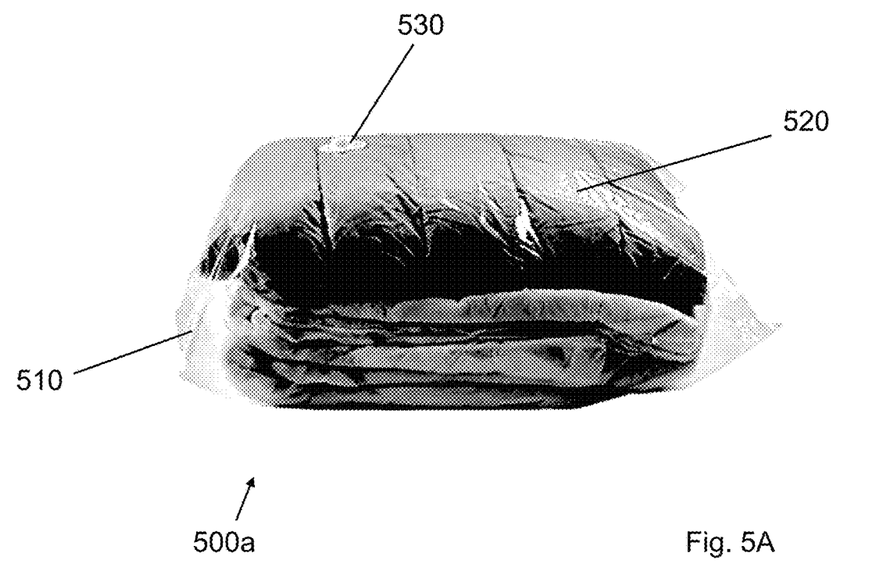
FIG. 5A illustrates an elevational view of a layer of product packaging in a non-evacuated state containing emergency preparedness items of a multipurpose emergency preparedness system in accordance with some embodiments of the present invention.
Figure 5B:
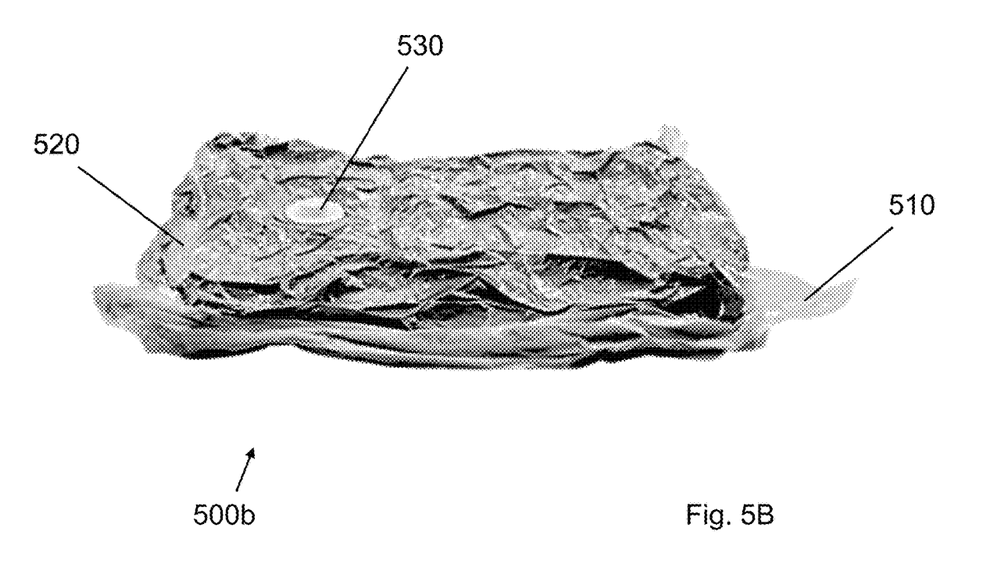
FIG. 5B illustrates an elevational view of a layer of product packaging in an evacuated state containing emergency preparedness items of a multipurpose emergency preparedness system in accordance with some embodiments of the present invention.

As shown in FIG. 5A, an elevational view of a layer of product packaging 500a in a non-evacuated state containing emergency preparedness items 520 of a multipurpose emergency preparedness system is provided. The layer of product packaging 500a may comprise an emergency preparedness item packaging layer 510, one or more emergency preparedness items 520 and a one-way vacuum valve 530. The emergency preparedness item packaging layer 510 may be utilized as a means of fluid-sealing one or more emergency preparedness items 520 in order to protect the sanitary use thereof. The one-way vacuum valve 530 may be utilized to manipulate the layer of product packaging 500a from the non-evacuated state to the evacuated state. As shown in FIG. 5B, an elevational view of a layer of product packaging 500b in an evacuated state containing emergency preparedness items 520 of a multipurpose emergency preparedness system is provided. FIG. 5 illustrates the transition of the layer of product packaging 500a from the non-evacuated state to the layer of product packaging 500b in the evacuated state. By utilizing vacuum-sealing, the one or more emergency preparedness items 520 may be compressed into a form factor that more easily fits into a cavity defined by an emergency kit packaging layer. Additionally, the emergency preparedness item packaging layer 510 may comprise an elongate resealable press seal closure disposed along an end portion thereof to allow a user to access the one or more emergency preparedness items 520.

The specification and drawings are to be regarded in an illustrative rather than a restrictive sense. However, it will be evident that various modifications and changes may be made thereunto without departing from the broader spirit and scope of the invention as set forth in the claims. Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

All features disclosed in the specification, claims, abstract, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent, or similar purpose, unless expressly stated otherwise.

Throughout this disclosure, the phrase 'modularly coupled' and similar terms and phrases are intended to convey that any element of a given class of elements may be coupled to another given element and vice versa with equal effect. For example, any extension cord of a plurality of extension cords may be modularly coupled to another extension cord and vice versa with equal effect. Further, throughout this disclosure, the phrase 'removably coupled' and similar terms and phrases are intended to convey that a given element may be iteratively coupled to and removed from another given element as desired. For example, a male plug of a first extension cord may be removably coupled to a female plug of a second extension cord as desired.

The use of the terms "a," "an," "the," and similar referents in the context of describing the disclosed embodiments (especially in the context of the following claims) are to be construed to cover both the singular and the plural, unless otherwise indicated or clearly contradicted by context. The terms "comprising," "having," "including," and "containing" are to be construed as open-ended terms (i.e., meaning "including, but not limited to,") unless otherwise noted. The term "coupled" or "connected," where unmodified and referring to physical connections, is to be construed as partly or wholly contained within, attached to, or joined together, even if there is something intervening. Recitation of ranges of values are merely intended to serve as a shorthand method of referring individually to each separate value falling within the range, unless otherwise indicated and each separate value is incorporated into the specification as if it were individually recited. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Conjunctive language, such as phrases of the form "at least one of A, B, and C," or "at least one of A, B and C," is understood with the context as used in general to present that an item, term, etc., may be either A or B or C, or any nonempty subset of the set of A and B and C, unless specifically stated otherwise or otherwise clearly contradicted by context. For instance, in the illustrative example of a set having three members, the conjunctive phrases "at least one of A, B, and C" and "at least one of A, B and C" refer to any of the following sets: {A}, {B}, {C}, {A, B}, {A, C}, {B, C}, {A, B, C}. Thus, such conjunctive language is not generally intended to imply that certain embodiments require at least one of A, at least one of B and at least one of C each to be present. In addition, unless otherwise noted or contradicted by context, the term "plurality" indicates a state of being plural (e.g., "a plurality of items" indicates multiple items). The number of items in a plurality is at least two, but can be more when so indicated either explicitly or by context.

The use of any examples, or exemplary language (e.g., "such as") provided, is intended merely to better illuminate embodiments of the invention and does not pose a limitation on the scope of the invention unless otherwise claimed. No language in the specification should be construed as indicating any non-claimed element as essential to the practice of the invention.

Embodiments of this disclosure are described, including the best mode known to the inventors for carrying out the invention. Variations of those embodiments may become apparent to those of ordinary skill in the art upon reading the foregoing description. The inventors expect skilled artisans to employ such variations as appropriate and the inventors intend for embodiments of the present disclosure to be practiced otherwise than as specifically described. Accordingly, the scope of the present disclosure includes all modifications and equivalents of the subject matter recited in the claims appended hereto as permitted by applicable law. Moreover, although above-described elements may be described in the context of certain embodiments of the specification, unless stated otherwise or otherwise clear from context, these elements are not mutually exclusive to only those embodiments in which they are described; any combination of the above-described elements in all possible variations thereof is encompassed by the scope of the present disclosure unless otherwise indicated or otherwise clearly contradicted by context.

All references, including publications, patent applications, and patents, cited are hereby incorporated by reference to the same extent as if each reference were individually and specifically indicated to be incorporated by reference and were set forth in its entirety.

The invention claimed is:

1. A multipurpose emergency preparedness system, comprising:
    an exterior packaging layer forming a fluid-tight seal around an inner packaging layer, wherein:
        the exterior packaging layer is fabricated at least partially from gelatin and seaweed;
        the inner packaging layer comprises a plurality of perimeter retaining walls defining one or more cavities therein;
    a plurality of survival kits disposed within the one or more cavities; and
    a plurality of emergency preparedness items disposed within each of the plurality of survival kits, wherein:
        each of the plurality of emergency preparedness items are disposed within an emergency preparedness item packaging layer, and
        the emergency preparedness item packaging layer is fabricated at least partially from gelatin and seaweed.

2. The multipurpose emergency preparedness system of claim 1, wherein the exterior packaging layer is fabricated from a transparent material.

3. The multipurpose emergency preparedness system of claim 1, wherein the exterior packaging layer is fabricated from a flexible material.

4. The multipurpose emergency preparedness system of claim 1, wherein the exterior packaging layer is fabricated from a biodegradable material having one or more alternative-use characteristics.

5. The multipurpose emergency preparedness system of claim 1, wherein the inner packaging layer is fabricated from an opaque material.

6. The multipurpose emergency preparedness system of claim 1, wherein the inner packaging layer is fabricated from a rigid material.

7. The multipurpose emergency preparedness system of claim 1, wherein the inner packaging layer is fabricated from a material comprising one or more medicinal compounds.

8. The multipurpose emergency preparedness system of claim 1, wherein the inner packaging layer is fabricated from a biodegradable material having one or more alternative-use characteristics.

9. The multipurpose emergency preparedness system of claim 1, wherein the plurality of perimeter retaining walls enclose a plurality of interior retaining walls.

10. The multipurpose emergency preparedness system of claim 9, wherein the plurality of interior retaining walls comprise a horizontal portion and a vertical portion.

11. The multipurpose emergency preparedness system of claim 1, wherein each of the plurality of survival kits comprise an emergency kit packaging layer.

12. The multipurpose emergency preparedness system of claim 11, wherein the emergency kit packaging layer is fabricated from a biodegradable material having one or more alternative-use characteristics.

13. The multipurpose emergency preparedness system of claim 11, wherein the emergency kit packaging layer encloses the plurality of emergency preparedness items.

14. The multipurpose emergency preparedness system of claim 11, wherein each of the plurality of survival kits comprise an emergency indicia element disposed upon an exterior surface of the emergency kit packaging layer.

15. The multipurpose emergency preparedness system of claim 1, wherein the plurality of survival kits comprise a land-based emergency kit comprising a water purification instrument, a metallic thermal blanket, a fire starter device, a fireproof covering element and a smoke filtering mask.

16. The multipurpose emergency preparedness system of claim 1, wherein the plurality of survival kits comprise a water-based emergency kit comprising an inflatable buoy device, a thermal blanket and a ginger food item.

17. The multipurpose emergency preparedness system of claim 1, wherein the plurality of survival kits comprise a fire-based emergency kit comprising a fireproof covering element and a smoke filtering mask.

18. The multipurpose emergency preparedness system of claim 1, wherein the plurality of survival kits comprise a flight-based emergency kit comprising an inflatable buoy device, a water purification instrument, a metallic thermal blanket, a fire starter device, a fireproof covering element, a ginger food item and a smoke filtering mask.

19. A multipurpose emergency preparedness system, comprising:
    an outer packaging layer forming a fluid-tight seal around an inner packaging layer, wherein:
        the outer packaging layer is fabricated at least partially from gelatin and seaweed;
        the inner packaging layer comprises a plurality of perimeter retaining walls defining one or more cavities therein, wherein the plurality of perimeter retaining walls enclose a plurality of interior retaining walls;
    a plurality of survival kits disposed within the one or more cavities, wherein:
        each of the plurality of survival kits comprise an emergency kit packaging layer, and each of the plurality of survival kits comprise an emergency indicia element disposed upon an exterior surface of the emergency kit packaging layer; and a plurality of emergency preparedness items disposed within each emergency kit packaging layer, wherein:
each of the plurality of emergency preparedness items are disposed within an emergency preparedness item packaging layer, and
the emergency preparedness item packaging layer is fabricated at least partially from gelatin and seaweed.

20. A multipurpose emergency preparedness system, comprising:
an outer packaging layer forming a fluid-tight seal around an inner packaging layer, wherein:
the outer packaging layer is fabricated at least partially from gelatin and seaweed;
the inner packaging layer comprises a plurality of perimeter retaining walls defining one or more cavities therein, wherein:
the plurality of perimeter retaining walls enclose a plurality of interior retaining walls,
the plurality of perimeter retaining walls and the plurality of interior retaining walls are each fabricated at least partially from hemp and mushroom byproduct, and
the plurality of interior retaining walls comprise a horizontal portion and a vertical portion;
a plurality of survival kits disposed within the one or more cavities, wherein:
each of the plurality of survival kits comprise an emergency kit packaging layer,
the emergency kit packaging layer is fabricated at least partially from coconut husks, and
each of the plurality of survival kits comprise an emergency indicia element disposed upon an exterior surface of the emergency kit packaging layer; and
a plurality of emergency preparedness items disposed within each emergency kit packaging layer, wherein:
each of the plurality of emergency preparedness items are disposed within an emergency preparedness item packaging layer,
the emergency preparedness item packaging layer is fabricated at least partially from gelatin and seaweed,
the emergency preparedness item packing layer forms a fluid-tight seal around one of the plurality of emergency preparedness items, and
the outer packaging layer, the plurality of perimeter retaining walls, the plurality of interior retaining walls, the emergency kit packaging layer, and the emergency preparedness item packaging layer collectively provide a caloric value at least 10 Joules per kilogram.

* * * * *